(12) United States Patent
Heiliger

(10) Patent No.: US 12,376,872 B2
(45) Date of Patent: *Aug. 5, 2025

(54) DRIVE MECHANISMS FOR SURGICAL INSTRUMENTS

(71) Applicant: Covidien LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 271 days.

This patent is subject to a terminal disclaimer.

(21) Appl. No.: 18/196,503

(22) Filed: May 12, 2023

(65) Prior Publication Data
US 2023/0277206 A1   Sep. 7, 2023

Related U.S. Application Data

(63) Continuation of application No. 16/785,910, filed on Feb. 10, 2020, now Pat. No. 11,648,023.

(51) Int. Cl.
*A61B 17/295* (2006.01)
*A61B 18/08* (2006.01)
(Continued)

(52) U.S. Cl.
CPC .......... *A61B 17/295* (2013.01); *A61B 18/085* (2013.01); *A61B 18/1445* (2013.01); *A61B 2017/00199* (2013.01); *A61B 2017/2936* (2013.01); *A61B 2017/320094* (2017.08); *A61B 2018/00077* (2013.01); *A61B 2018/0063* (2013.01); *A61B 2018/1807* (2013.01); *A61B 2018/1861* (2013.01);
(Continued)

(58) Field of Classification Search
CPC . A61B 17/295; A61B 18/085; A61B 18/1445; A61B 2017/320094; A61B 2018/1455; A61B 2018/1457
See application file for complete search history.

(56) References Cited

U.S. PATENT DOCUMENTS 5,752,973 A   5/1998   Kieturakis
5,792,135 A   8/1998   Madhani et al.
(Continued)

FOREIGN PATENT DOCUMENTS

EP   1915966 A1   4/2008

OTHER PUBLICATIONS

Extended European Search Report issued in corresponding application EP 21154685.8 dated Jun. 14, 2021, 8 pages.

*Primary Examiner* — Majid Jamialahmadi

(57) ABSTRACT

A surgical instrument for use with a robotic surgical system includes a knife blade configured to cut tissue and a knife tube coupled to the knife blade and configured to translate to move the knife blade for cutting tissue. The surgical instrument also includes a gearbox assembly coupleable to a robotic surgical system and configured to translate the knife tube to move the knife blade for cutting tissue and a knife blade lock operably coupled to the gearbox assembly. The knife blade lock is movable from a locked position wherein the knife blade lock prevents translation of the knife tube to an unlocked position in response to coupling of the gearbox assembly to the robotic surgical system wherein the knife tube is permitted to translate to move the knife blade for cutting tissue.

16 Claims, 11 Drawing Sheets

(51) Int. Cl.
    *A61B 18/14*     (2006.01)
    *A61B 17/00*     (2006.01)
    *A61B 17/29*     (2006.01)
    *A61B 17/32*     (2006.01)
    *A61B 18/00*     (2006.01)
    *A61B 18/18*     (2006.01)
    *A61B 34/00*     (2016.01)
    *A61B 34/35*     (2016.01)

(52) U.S. Cl.
    CPC ......... *A61B 2034/256* (2016.02); *A61B 34/35* (2016.02); *A61B 34/71* (2016.02)

(56) References Cited

U.S. PATENT DOCUMENTS

| | | |
|---|---|---|
| 5,848,986 A | 12/1998 | Lundquist et al. |
| 6,579,176 B2 | 6/2003 | Wen et al. |
| 6,817,974 B2 | 11/2004 | Cooper et al. |
| 7,799,028 B2 | 9/2010 | Schechter et al. |
| 7,861,906 B2 | 1/2011 | Doll et al. |
| 7,918,230 B2 | 4/2011 | Whitman et al. |
| 8,579,176 B2 | 11/2013 | Smith et al. |
| 9,055,961 B2 | 6/2015 | Manzo et al. |
| 9,474,569 B2 | 10/2016 | Manzo et al. |
| 11,648,023 B2 | 5/2023 | Heiliger |
| 2002/0099371 A1 | 7/2002 | Schulze et al. |
| 2002/0177842 A1 | 11/2002 | Weiss |
| 2003/0125734 A1 | 7/2003 | Mollenauer |
| 2003/0208186 A1 | 11/2003 | Moreyra |
| 2004/0049205 A1 | 3/2004 | Lee et al. |
| 2006/0022015 A1 | 2/2006 | Shelton et al. |
| 2006/0025811 A1 | 2/2006 | Shelton |
| 2007/0233052 A1 | 10/2007 | Brock |
| 2008/0015631 A1 | 1/2008 | Lee et al. |
| 2010/0274265 A1 | 10/2010 | Wingardner et al. |
| 2010/0292691 A1 | 11/2010 | Brogna |
| 2011/0015650 A1 | 1/2011 | Choi et al. |
| 2011/0118707 A1 | 5/2011 | Burbank |
| 2011/0118708 A1 | 5/2011 | Burbank et al. |
| 2011/0118709 A1 | 5/2011 | Burbank |
| 2011/0118754 A1 | 5/2011 | Dachs, II et al. |
| 2014/0005654 A1 | 1/2014 | Batross et al. |
| 2016/0184037 A1 | 6/2016 | Cooper et al. |
| 2016/0262826 A1* | 9/2016 | Allen, IV ............ A61B 17/295 |
| 2017/0252096 A1 | 9/2017 | Felder et al. |
| 2017/0348063 A1 | 12/2017 | Braun et al. |
| 2018/0008338 A1 | 1/2018 | Kopp |
| 2018/0353179 A1 | 12/2018 | Shelton, IV et al. |

\* cited by examiner

DRIVE MECHANISMS FOR SURGICAL INSTRUMENTS

CROSS-REFERENCE TO RELATED APPLICATIONS

This application is a continuation of U.S. patent application Ser. No. 16/785,910, filed on Feb. 10, 2020, now U.S. Pat. No. 11,648,023.

INTRODUCTION

The present disclosure relates to surgical instruments and, more specifically, to drive mechanisms for surgical instruments for use in robotic surgical systems.

BACKGROUND

Robotic surgical systems are increasingly utilized in various surgical procedures. Some robotic surgical systems include a console supporting a robotic arm. One or more different surgical instruments may be configured for use with the robotic surgical system and selectively mountable to the robotic arm. The robotic arm provides one or more inputs to the mounted surgical instrument to enable operation of the mounted surgical instrument.

The number, type, and configuration of inputs provided by the robotic arm of a robotic surgical system are constraints in the design of surgical instruments configured for use with the robotic surgical system. That is, in designing a surgical instrument compatible for mounting on and use with the robotic arm of a robotic surgical system, consideration should be given to determining how to utilize the available inputs provided by the robotic arm to achieve the desired functionality of the surgical instrument.

SUMMARY

As used herein, the term "distal" refers to the portion that is being described which is further from a surgeon, while the term "proximal" refers to the portion that is being described which is closer to a surgeon. The terms "about," substantially," and the like, as utilized herein, are meant to account for manufacturing, material, environmental, use, and/or measurement tolerances and variations. Further, to the extent consistent, any of the aspects described herein may be used in conjunction with any or all of the other aspects described herein.

Provided in accordance with aspects of the present disclosure is a surgical instrument for use with a robotic surgical system. The surgical instrument includes a housing, a shaft extending distally from the housing, and an end effector assembly extending distally from the shaft. The end effector assembly includes first and second jaw members. At least the first jaw member is movable relative to the second jaw member from a spaced-apart position to an approximated position to grasp tissue therebetween. The surgical instrument also includes a knife blade configured to cut tissue and a knife tube coupled to the knife blade and extending from the housing through the shaft. The knife tube is configured to translate to move the knife blade between the first and second jaw members for cutting tissue grasped therebetween. The surgical instrument also includes a gearbox assembly disposed within the housing. The gearbox assembly includes a drive input configured to receive a rotational input from a robotic surgical system and an input shaft operably coupled to the drive input and the knife tube. The drive input is configured to drive rotation of the input shaft in response to rotational input received by the drive input to translate the knife tube. The surgical instrument also includes a knife blade lock operably coupled to the drive input of the gearbox assembly. The knife blade lock is movable between a locked position wherein the knife blade lock engages the drive input to prevent rotation of the drive input and an unlocked position wherein the knife lock is disengaged from the drive input such that the drive input is permitted to rotate in response to receiving the rotational input.

In an aspect of the present disclosure, the surgical instrument includes a biasing member disposed within the housing and operably coupled to the knife blade lock. The biasing member is configured to bias the knife blade lock into the locked position.

In another aspect of the present disclosure, the knife blade lock includes a plurality of protrusions extending from an annular body portion.

In another aspect of the present disclosure, the annular body portion of the knife blade lock defines a plurality of teeth configured to interlock with a plurality of teeth defined by the drive input when the knife blade lock is in the locked position.

In yet another aspect of the present disclosure, the plurality of protrusions extends distally from a distal end of the housing when the knife blade lock is in the locked position.

In still another aspect of the present disclosure, the plurality of protrusions extends through an aperture defined through a proximal end of the housing.

In still yet another aspect of the present disclosure, the drive input includes at least one distally extending finger disposed through an aperture defined by the annular body portion of the knife blade lock.

In another aspect of the present disclosure, the knife blade lock is configured to be contacted and moved distally by an instrument interface of the robotic surgical system upon coupling of the surgical instrument to the robotic surgical system to move the knife blade lock to the unlocked position.

In another aspect of the present disclosure, the gearbox assembly includes an input gear, a central gear, and a lead screw. The input gear is engaged to a distal end portion of the input shaft. Rotational input provided to the drive input drives rotation of the input shaft when the knife blade lock is in the unlocked position to drive rotation of the input gear. The central gear defines an internal threading and an external threading in meshed engagement with the input gear. The lead screw extends through the central gear and is threadingly engaged with the internal threading of the central gear. Rotation of the central gear in response to rotational input provided to the drive input translates the lead screw to translate the knife tube, thereby moving the knife blade between the first and second jaw members.

Also provided in accordance with aspects of the present disclosure is a surgical instrument for use with a robotic surgical system including a knife blade configured to cut tissue, a knife tube coupled to the knife blade and configured to translate to move the knife blade for cutting tissue, and a gearbox assembly. The gearbox assembly includes a drive input configured to receive a rotational input from a robotic surgical system and an input shaft operably coupled to the drive input and the knife tube. The drive input is configured to drive rotation of the input shaft in response to rotational input received by the drive input to translate the knife tube. The surgical instrument also includes a knife blade lock operably coupled to the drive input of the gearbox assembly.

The knife blade lock is movable between a locked position wherein the knife blade lock engages the drive input to prevent rotation of the drive input and an unlocked position wherein the knife lock is disengaged from the drive input such that the drive input is permitted to rotate in response to receiving the rotational input to translate the knife tube and move the knife blade.

In an aspect of the present disclosure, the surgical instrument includes a biasing member operably coupled to the knife blade lock and configured to bias the knife blade lock into the locked position.

In another aspect of the present disclosure, the knife blade lock includes a plurality of protrusions extending from an annular body portion.

In another aspect of the present disclosure, the annular body portion of the knife blade lock defines a plurality of teeth configured to interlock with a plurality of teeth defined by the drive input when the knife blade lock is in the locked position.

In yet another aspect of the present disclosure, the drive input includes at least one distally extending finger disposed through an aperture defined by the annular body portion of the knife blade lock.

In still another aspect of the present disclosure, the knife blade lock is configured to be contacted and moved distally by an instrument interface of the robotic surgical system upon coupling of the surgical instrument to the robotic surgical system to move the knife blade lock to the unlocked position.

In still yet another aspect of the present disclosure, the gearbox assembly includes and input gear, a central gear, and a lead screw. The input gear is engaged to a distal end portion of the input shaft, wherein rotational input provided to the drive input drives rotation of the input shaft when the knife blade lock is in the unlocked position to drive rotation of the input gear. The central gear defines an internal threading and an external threading in meshed engagement with the input gear. The lead screw extends through the central gear and is threadingly engaged with the internal threading of the central gear, wherein rotation of the central gear in response to rotational input provided to the drive input translates the lead screw to translate the knife tube, thereby moving the knife blade to cut tissue.

Also provided in accordance with aspects of the present disclosure is a surgical instrument for use with a robotic surgical system including a knife blade configured to cut tissue and a knife tube coupled to the knife blade and configured to translate to move the knife blade for cutting tissue. The surgical instrument also includes a gearbox assembly coupleable to a robotic surgical system and configured to translate the knife tube to move the knife blade for cutting tissue and a knife blade lock operably coupled to the gearbox assembly. The knife blade lock is movable from a locked position wherein the knife blade lock prevents translation of the knife tube to an unlocked position in response to coupling of the gearbox assembly to the robotic surgical system wherein the knife tube is permitted to translate to move the knife blade for cutting tissue.

In an aspect of the present disclosure, the gearbox assembly includes a drive input configured to receive a rotational input from the robotic surgical system and an input shaft operably coupled to the drive input and the knife tube. The drive input is configured to drive rotation of the input shaft in response to rotational input received by the drive input to translate the knife tube.

In another aspect of the present disclosure, the gearbox assembly includes an input gear, a central gear, and a lead screw. The input gear is engaged to a distal end portion of the input shaft. Rotational input provided to the drive input drives rotation of the input shaft when the knife blade lock is in the unlocked position to drive rotation of the input gear. The central gear defines an internal threading and an external threading in meshed engagement with the input gear. The lead screw extends through the central gear and is threadingly engaged with the internal threading of the central gear. Rotation of the central gear in response to rotational input provided to the drive input translates the lead screw to translate the knife tube, thereby moving the knife blade to cut tissue.

In yet another aspect of the present disclosure, the knife blade lock defines a plurality of teeth configured to interlock with a plurality of teeth defined by the drive input when the knife blade lock is in the locked position.

BRIEF DESCRIPTION OF THE DRAWINGS

Various aspects and features of the present disclosure are described hereinbelow with reference to the drawings wherein like numerals designate identical or corresponding elements in each of the several views.

DETAILED DESCRIPTION

Figure 1A:
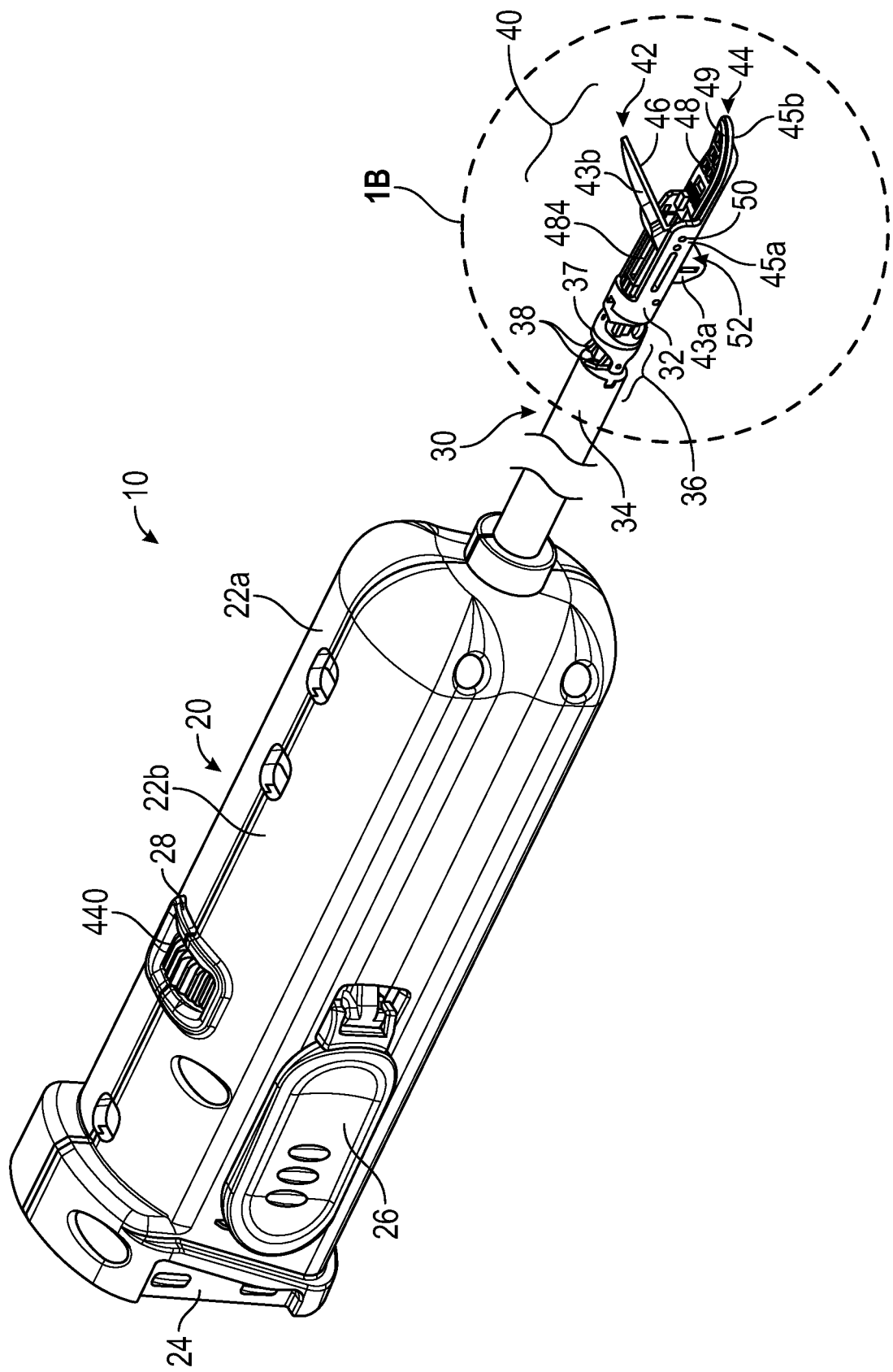
FIG. 1A is a perspective view of a surgical instrument provided in accordance with the present disclosure configured for mounting on a robotic arm of a robotic surgical system.

Referring to FIGS. 1A-3, a surgical instrument 10 provided in accordance with the present disclosure generally includes a housing 20, a shaft 30 extending distally from housing 20, an end effector assembly 40 extending distally from shaft 30, and a gearbox assembly 100 disposed within housing 20 and operably associated with end effector assembly 40. Instrument 10 is detailed herein as an articulating electrosurgical forceps configured for use with a robotic surgical system, e.g., robotic surgical system 1000 (FIG. 4). However, the aspects and features of instrument 10 provided in accordance with the present disclosure, detailed below, are equally applicable for use with other suitable surgical instruments and/or in other suitable surgical systems.

With particular reference to FIG. 1A, housing 20 of instrument 10 includes first and second body portion 22a, 22b and a proximal face plate 24 that cooperate to enclose gearbox assembly 100 therein. Proximal face plate 24 includes apertures defined therein through which drive inputs 110-140 of gearbox assembly 100 extend. A pair of latch levers 26 (only one of which is illustrated in FIG. 1) extending outwardly from opposing sides of housing 20 enable releasable engagement of housing 20 with a robotic arm of a surgical system, e.g., robotic surgical system 1000 (FIG. 4). An aperture 28 defined through housing 20 permits thumbwheel 440 to extend therethrough to enable manual manipulation of thumbwheel 440 from the exterior of housing 20 to, as detailed below, permit manual opening and closing of end effector assembly 40.

Shaft 30 of instrument 10 includes a distal segment 32, a proximal segment 34, and an articulating section 36 disposed between the distal and proximal segments 32, 34, respectively. Articulating section 36 includes one or more articulating components 37, e.g., links, joints, etc. A plurality of articulation cables 38, e.g., four (4) articulation cables, or other suitable actuators, extend through articulating section 36. More specifically, articulation cables 38 are operably coupled to distal segment 32 of shaft 30 at the distal ends thereof and extend proximally from distal segment 32 of shaft 30, through articulating section 36 of shaft 30 and proximal segment 34 of shaft 30, and into housing 20, wherein articulation cables 38 operably couple with an articulation sub-assembly 200 of gearbox assembly 100 to enable selective articulation of distal segment 32 (and, thus end effector assembly 40) relative to proximal segment 34 and housing 20, e.g., about at least two axes of articulation (yaw and pitch articulation, for example). Articulation cables 38 are arranged in a generally rectangular configuration, although other suitable configurations are also contemplated.

With respect to articulation of end effector assembly 40 relative to proximal segment 34 of shaft 30, articulation cables 38 are actuated in pairs. More specifically, in order to pitch end effector assembly 40, the upper pair of cables 38 are actuated in a similar manner while the lower pair of cables 38 are actuated in a similar manner relative to one another but an opposite manner relative to the upper pair of cables 38. With respect to yaw articulation, the right pair of cables 38 are actuated in a similar manner while the left pair of cables 38 are actuated in a similar manner relative to one another but an opposite manner relative to the right pair of cables 38.

Figure 1B:
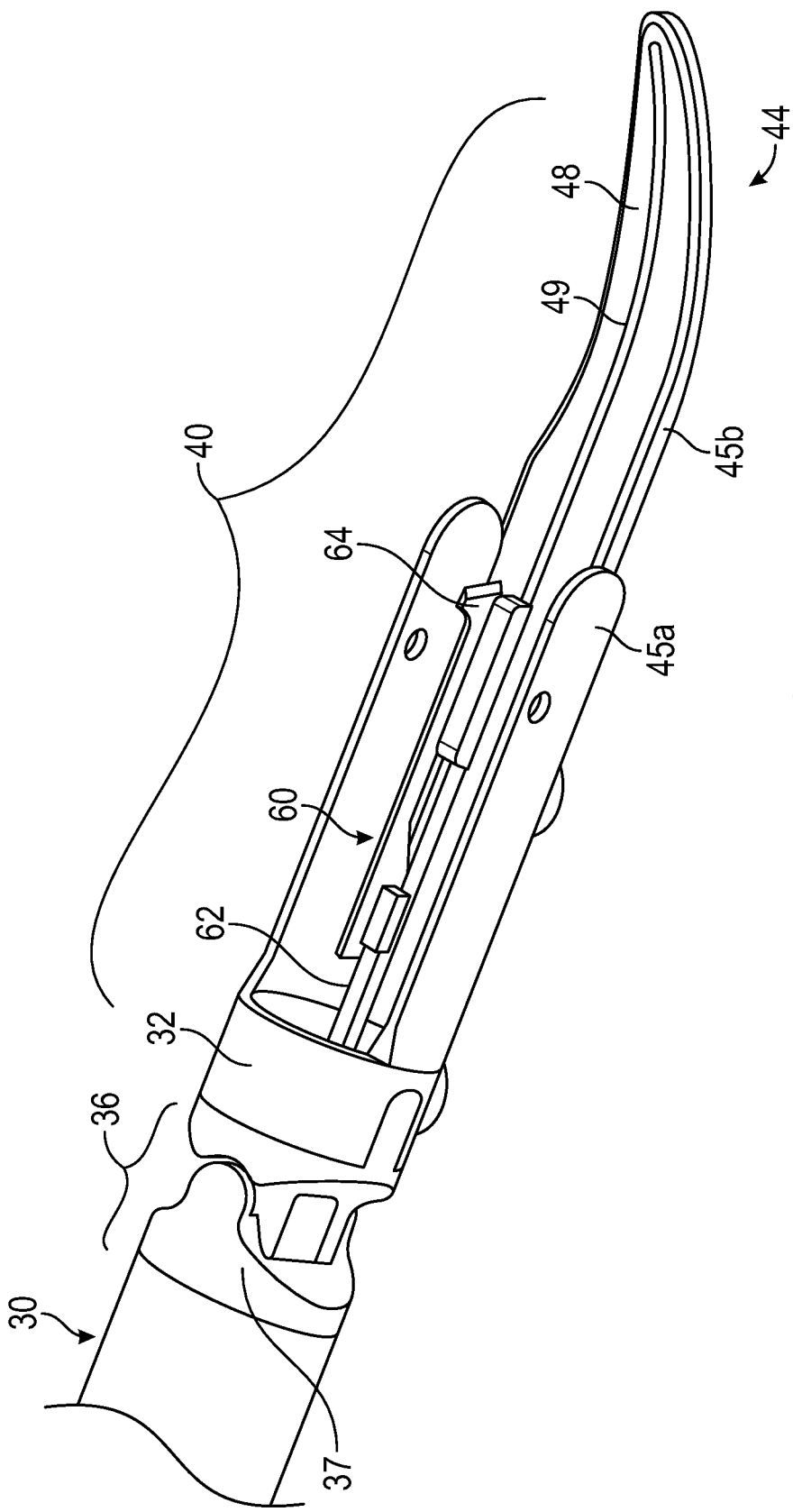
FIG. 1B is an enlarged, perspective view of the area of detail indicated as "1B" in FIG. 1A, illustrating an end effector assembly of the surgical instrument of FIG. 1A with one of the jaw members thereof removed.

With reference to FIGS. 1A and 1B, end effector assembly 40 includes first and second jaw members 42, 44, respectively. Each jaw member 42, 44 includes a proximal flange portion 43a, 45a and a distal body portion 43b, 45b, respectively. Distal body portions 43b, 45b define opposed tissue-contacting surfaces 46, 48, respectively. Proximal flange portions 43a, 45a are pivotably coupled to one another about a pivot 50 and are operably coupled to one another via a cam-slot assembly 52 including a cam pin slidably received within cam slots defined within the proximal flange portion 43a, 45a of at least one of the jaw members 42, 44, respectively, to enable pivoting of jaw member 42 relative to jaw member 44 and distal segment 32 of shaft 30 between a spaced-apart position (e.g., an open position of end effector assembly 40) and an approximated position (e.g. a closed position of end effector assembly 40) for grasping tissue between tissue-contacting surfaces 46, 48. As an alternative to this unilateral configuration, a bilateral configuration may be provided whereby both jaw members 42, 44 are pivotable relative to one another and distal segment 32 of shaft 30.

Longitudinally-extending knife channels 49 (only knife channel 49 of jaw member 44 is illustrated; the knife channel of jaw member 42 is similarly configured) are defined through tissue-contacting surfaces 46, 48, respectively, of jaw members 42, 44. A knife assembly 60 including a knife tube 62 extending from housing 20 through shaft 30 to end effector assembly 40 and a knife blade 64 disposed within end effector assembly 40 between jaw members 42, 44 is provided to enable cutting of tissue grasped between tissue-contacting surfaces 46, 48 of jaw members 42, 44, respectively. Knife tube 62 is operably coupled to a knife drive sub-assembly 300 of gearbox assembly 100 (FIGS. 2A-2B) at a proximal end thereof to enable selective actuation thereof to, in turn, move the knife blade 64 (e.g., longitudinally along a longitudinal axis defined by shaft 30) between jaw members 42, 44 to cut tissue grasped between tissue-contacting surfaces 46, 48.

Referring still to FIG. 1A, a drive rod 484 is operably coupled to cam-slot assembly 52 of end effector assembly 40, e.g., engaged with the cam pin thereof, such that longitudinal actuation of drive rod 484 pivots jaw member 42 relative to jaw member 44 between the spaced-apart and approximated positions. More specifically, urging drive rod 484 proximally pivots jaw member 42 relative to jaw member 44 towards the approximated position while urging drive rod 484 distally pivots jaw member 42 relative to jaw member 44 towards the spaced-apart position. However, other suitable mechanisms and/or configurations for pivoting jaw member 42 relative to jaw member 44 between the spaced-apart and approximated positions in response to selective actuation of drive rod 484 are also contemplated. Drive rod 484 extends proximally from end effector assembly 40 through shaft 30 and into housing 20 wherein drive rod 484 is operably coupled with a jaw drive sub-assembly 400 of gearbox assembly 100 (FIGS. 2A-2B) to enable selective actuation of end effector assembly 40 to grasp tissue therebetween.

Tissue-contacting surfaces 46, 48 of jaw members 42, 44, respectively, are at least partially formed from an electrically conductive material and are energizable to different potentials to enable the conduction of electrical energy through tissue grasped therebetween, although tissue-contacting surfaces 46, 48 may alternatively be configured to supply any suitable energy, e.g., thermal, microwave, light, ultrasonic, ultrasound, etc., through tissue grasped therebetween for energy-based tissue treatment. Instrument 10 defines a conductive pathway (not shown) through housing 20 and shaft 30 to end effector assembly 40 that may include lead wires, contacts, and/or electrically-conductive components to enable electrical connection of tissue-contacting surfaces 46, 48 of jaw members 42, 44, respectively, to an energy source (not shown), e.g., an electrosurgical generator, for supplying energy to tissue-contacting surfaces 46, 48 to treat, e.g., seal, tissue grasped between tissue-contacting surfaces 46, 48.

Figure 2A:
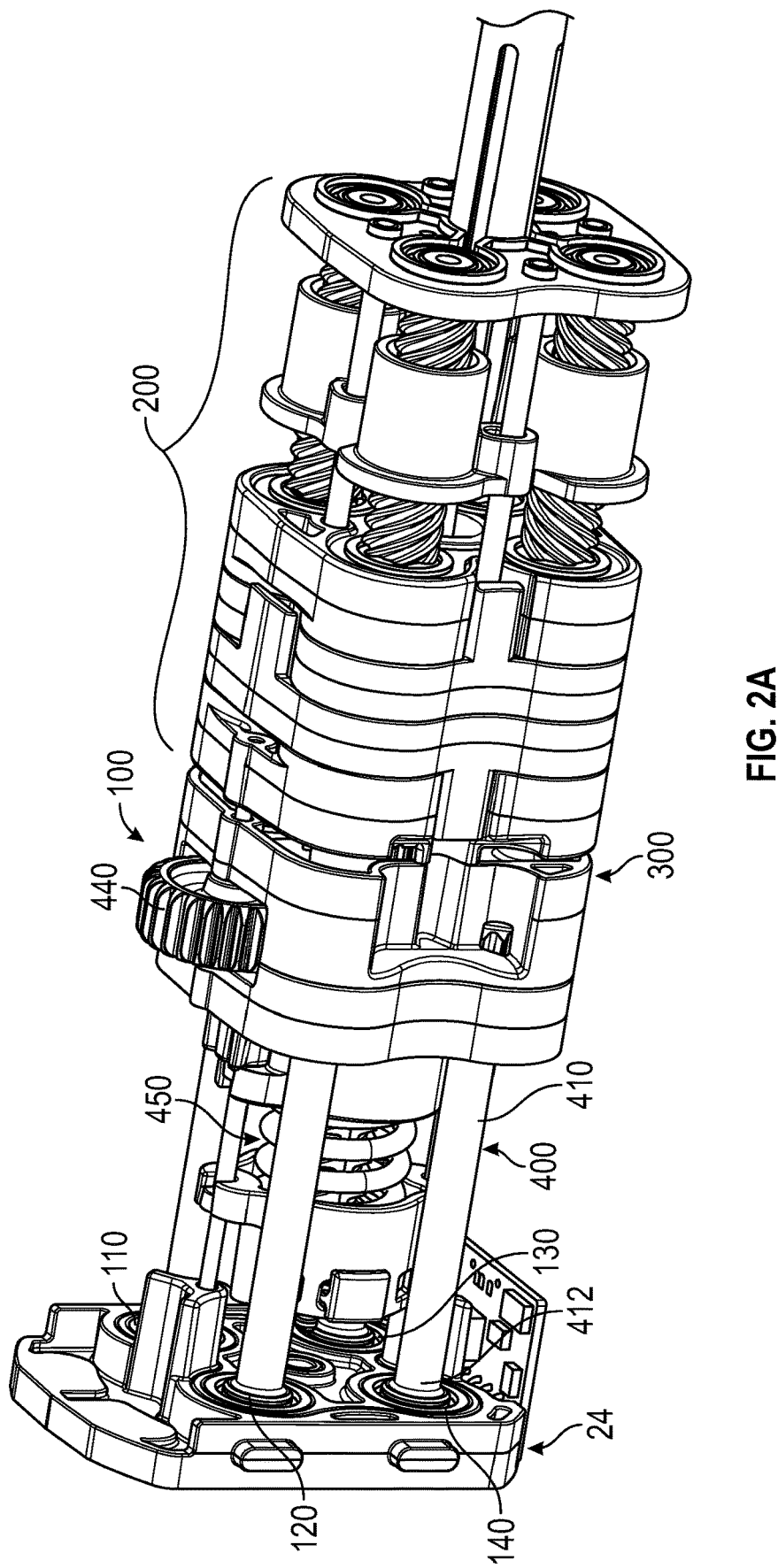
FIG. 2A is a front, perspective view of a proximal portion of the surgical instrument of FIG. 1A with an outer shell removed.
Figure 2B:
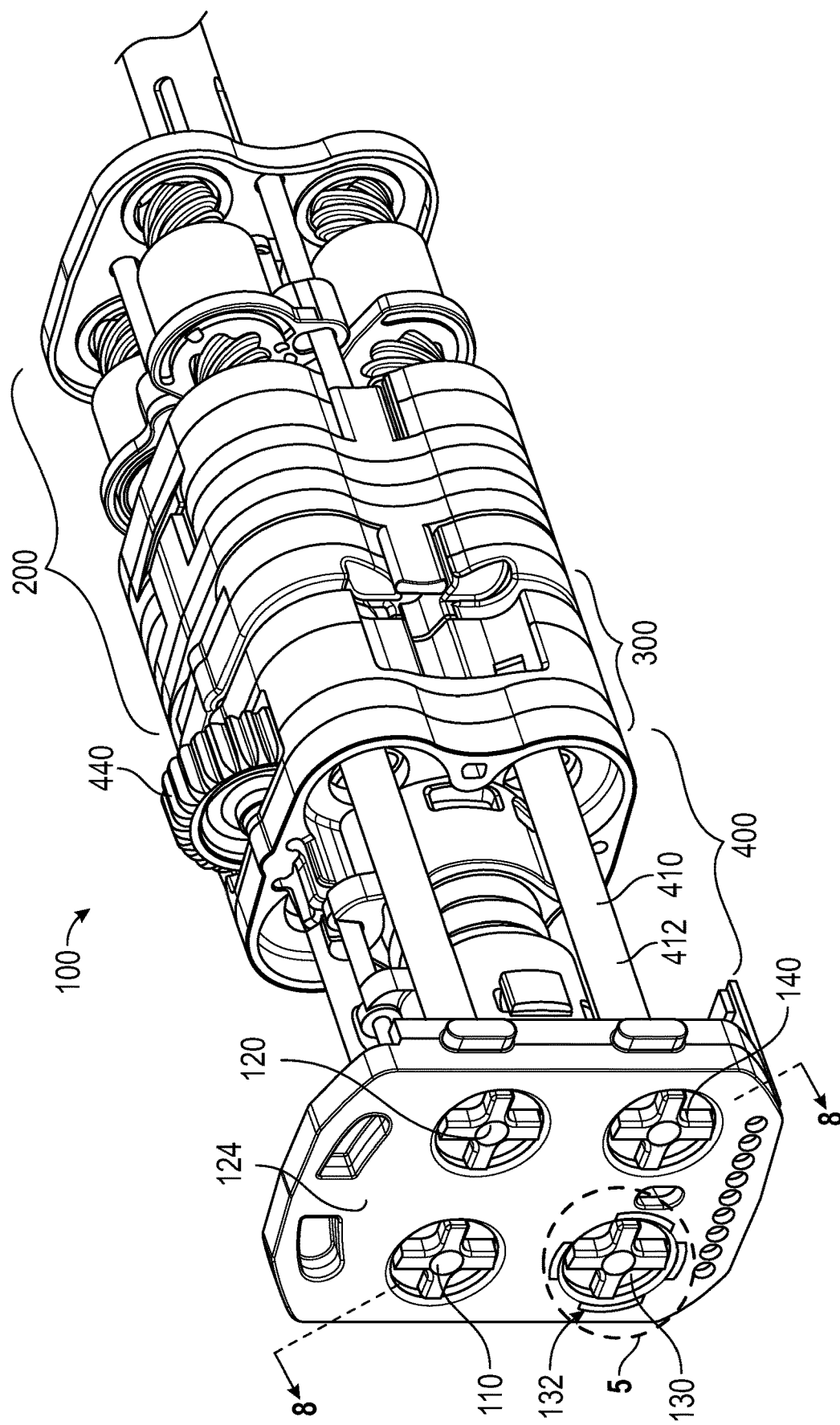
FIG. 2B is a rear, perspective view of the proximal portion of the surgical instrument of FIG. 1 with the outer shell removed.
Figure 3:
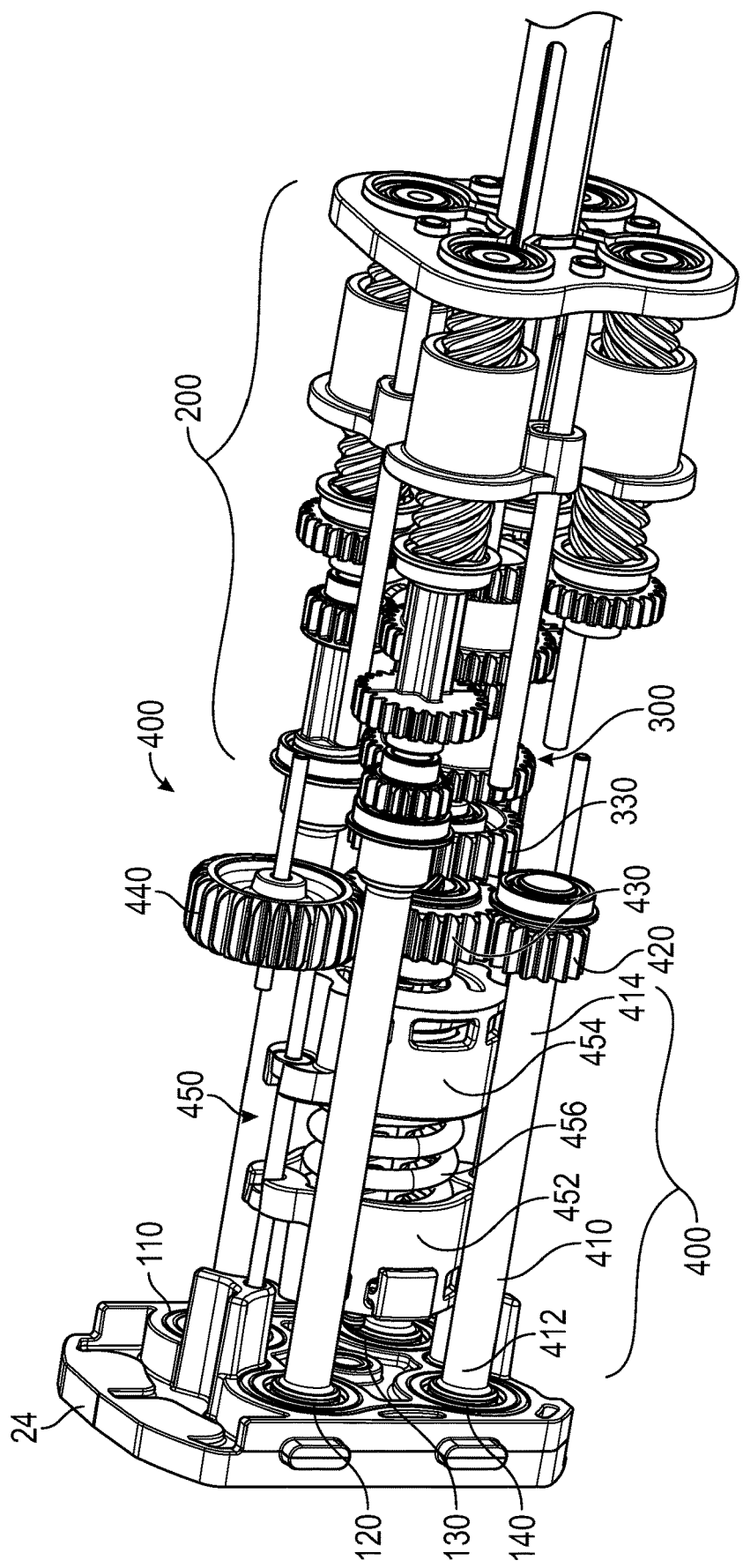
FIG. 3 is a front, perspective view of the proximal portion of the surgical instrument of FIG. 1 with the outer shell and additional internal components removed.
Figure 4:
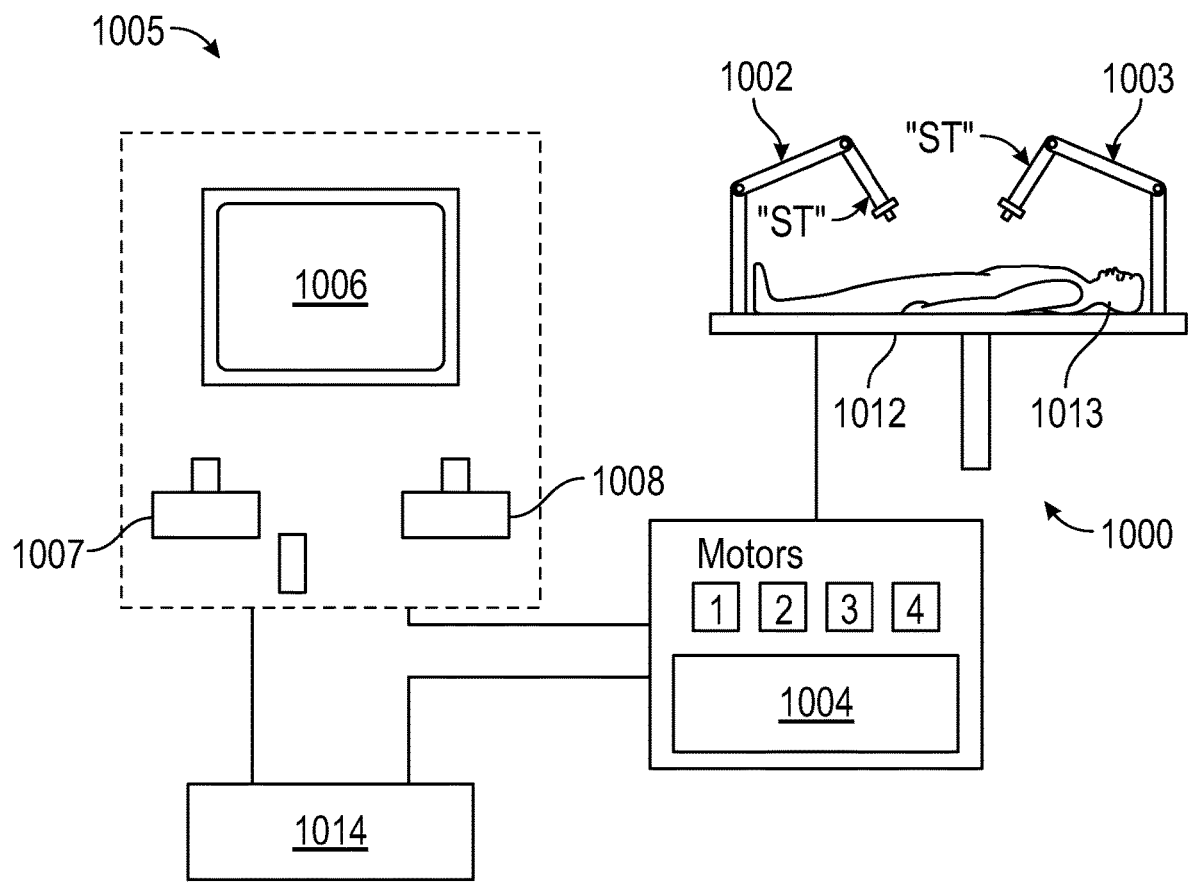
FIG. 4 is a schematic illustration of an exemplary robotic surgical system configured to releasably receive the surgical instrument of FIG. 1.
Figure 5:
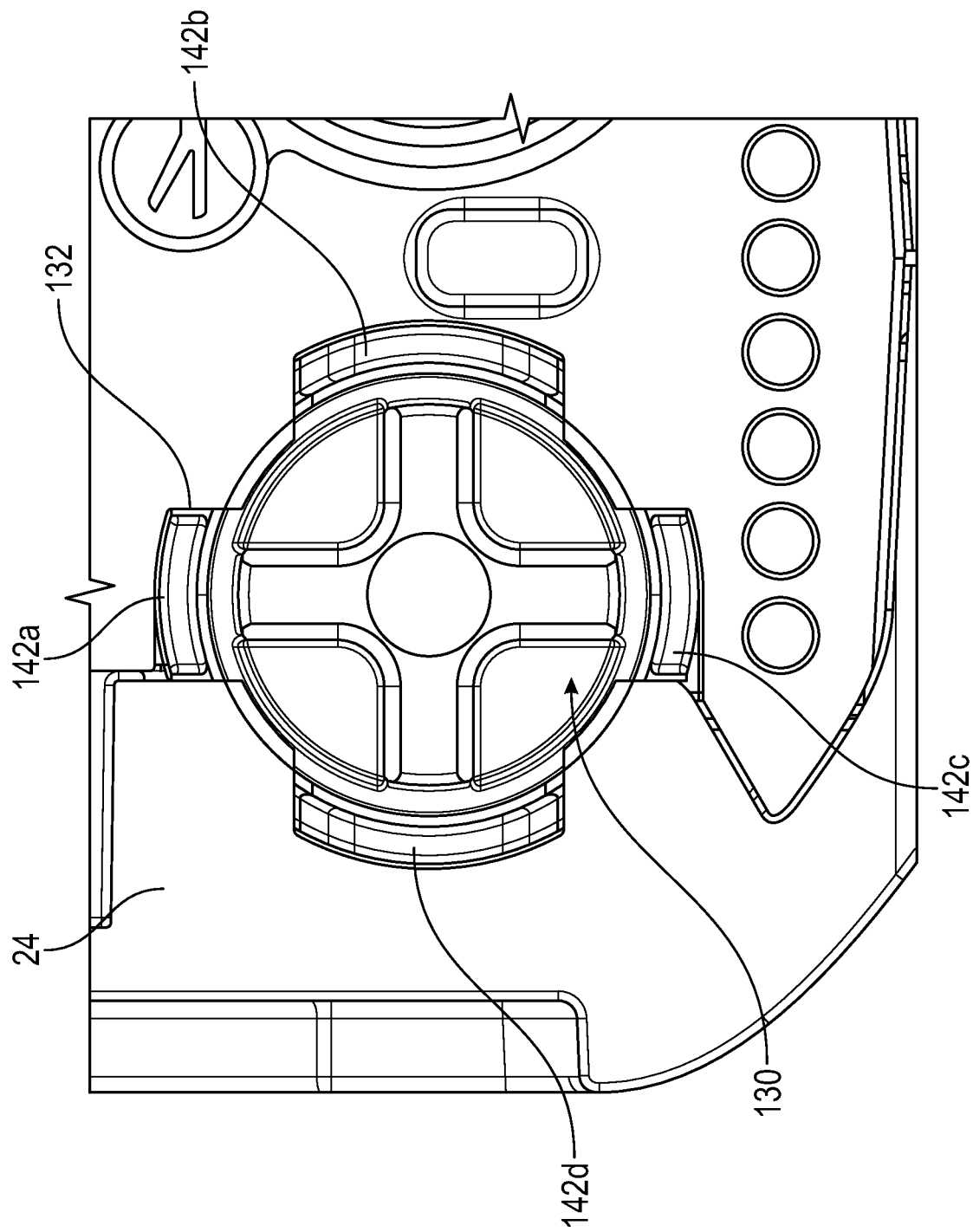
FIG. 5 is an enlarged, perspective view of the area of detail "5" in FIG. 2B.
Figure 6:
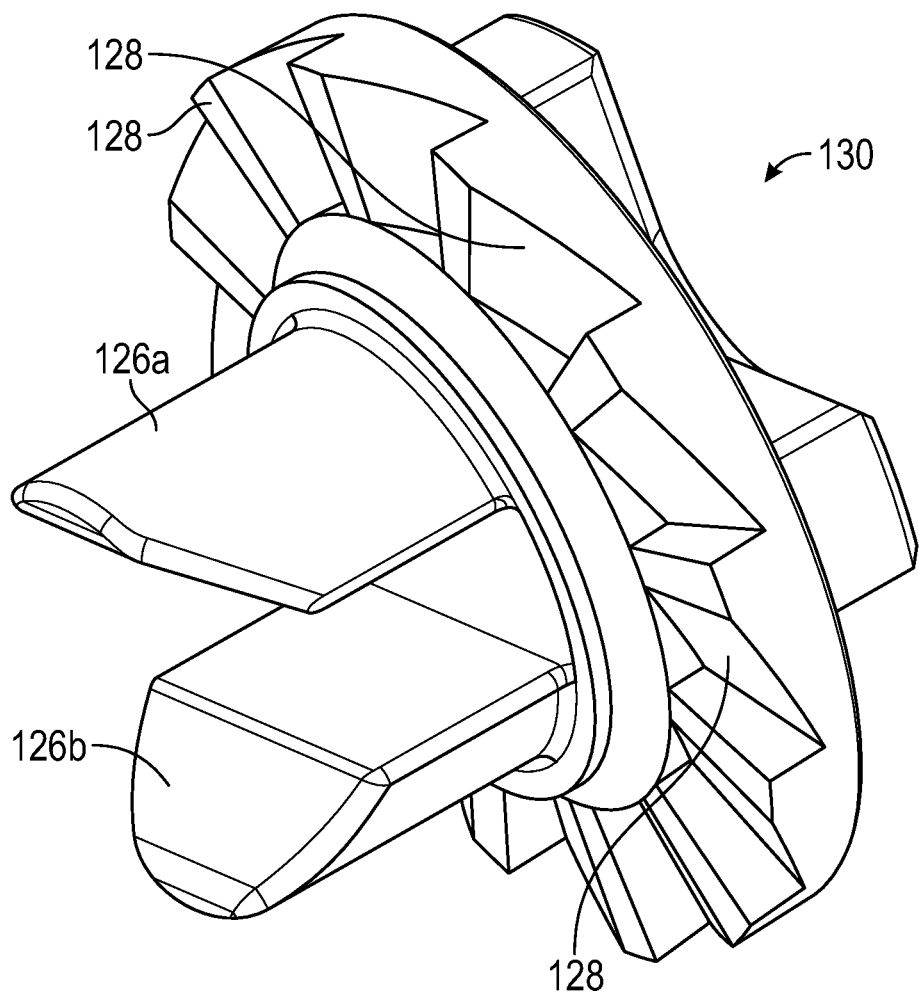
FIG. 6 is an enlarged, perspective view illustrating a drive input of the surgical instrument of FIG. 1.
Figure 7:
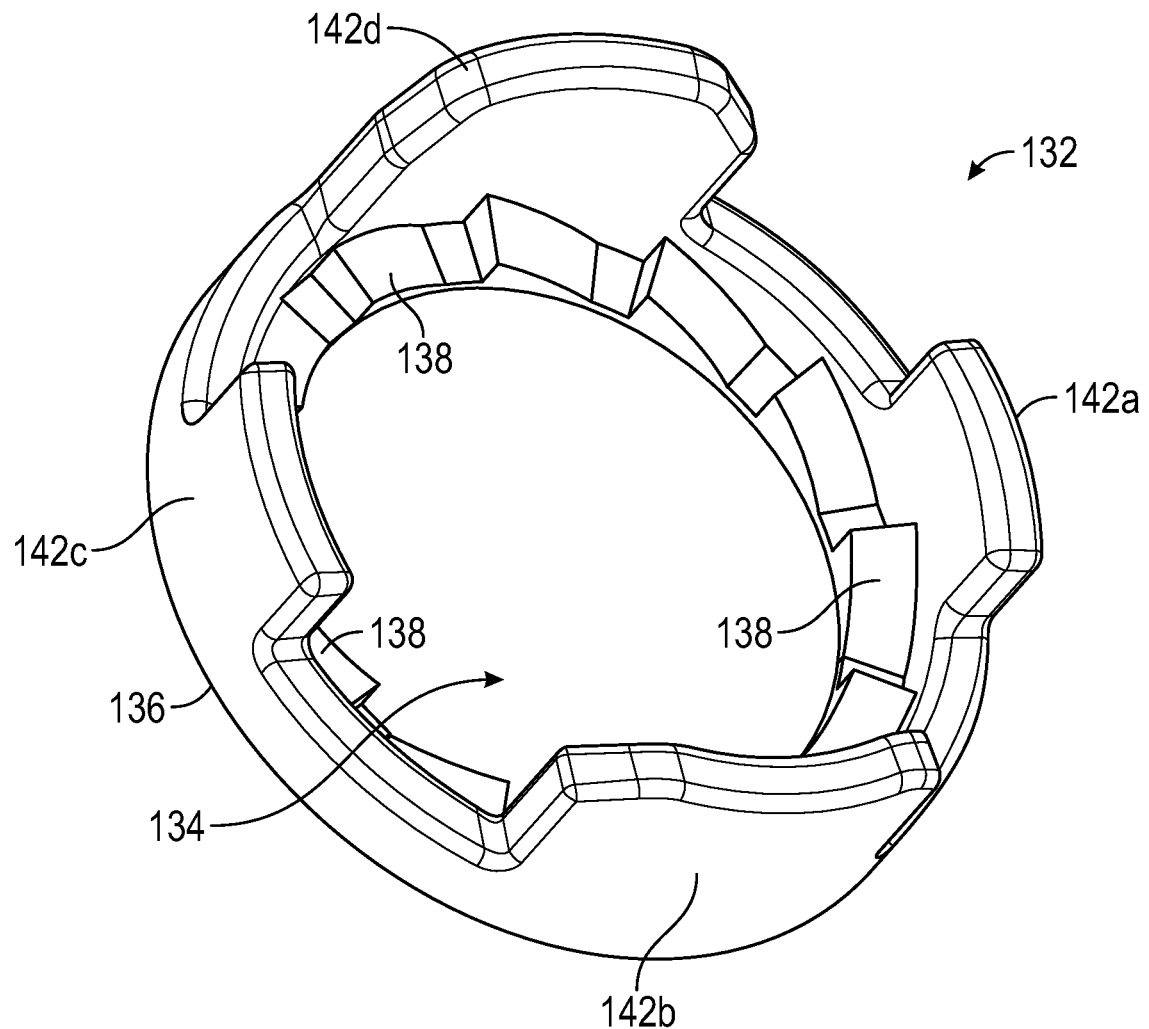
FIG. 7 is an enlarged, perspective view illustrating a knife blade lock of the surgical instrument of FIG. 1.

With additional reference to FIGS. 2A, 2B, and 3, gearbox assembly 100 is disposed within housing 20 and includes an articulation sub-assembly 200, a knife drive sub-assembly 300, and a jaw drive sub-assembly 400. Articulation sub-assembly 200 is operably coupled between first and second drive inputs 110, 120, respectively, of gearbox assembly 100 and articulation cables 38 (FIG. 1A) such that, upon receipt of appropriate inputs into first and/or second drive inputs 110, 120, articulation sub-assembly 200 manipulates cables 38 (FIG. 1A) to articulate end effector assembly 40 in a desired direction, e.g., to pitch and/or yaw end effector assembly 40.

Knife drive sub-assembly 300 is operably coupled between third drive input 130 of gearbox assembly 100 and knife tube 62 such that, upon receipt of appropriate input into third drive input 130, knife drive sub-assembly 300 manipulates knife tube 62 to move knife blade 64 (FIG. 1B) between jaw members 42, 44 to cut tissue grasped between tissue-contacting surfaces 46, 48.

Jaw drive sub-assembly 400 is operably coupled between fourth drive input 140 of gearbox assembly 100 and drive rod 484 such that, upon receipt of appropriate input into fourth drive input 140, jaw drive sub-assembly 400 pivots jaw members 42, 44 between the spaced-apart and approximated positions to grasp tissue therebetween.

Gearbox assembly 100 is configured to operably interface with a robotic surgical system 1000 (FIG. 4) when instrument 10 is mounted on robotic surgical system 1000 (FIG. 4), to enable robotic operation of gearbox assembly 100 to provide the above-detailed functionality. That is, robotic surgical system 1000 (FIG. 4) selectively provides inputs to drive inputs 110-140 of gearbox assembly 100 to articulate end effector assembly 40, grasp tissue between jaw members 42, 44, and/or cut tissue grasped between jaw members 42, 44. However, it is also contemplated that gearbox assembly 100 be configured to interface with any other suitable surgical system, e.g., a manual surgical handle, a powered surgical handle, etc. For the purposes herein, robotic surgical system 1000 (FIG. 4) is generally described.

Turning to FIG. 4, robotic surgical system 1000 is configured for use in accordance with the present disclosure. Aspects and features of robotic surgical system 1000 not germane to the understanding of the present disclosure are omitted to avoid obscuring the aspects and features of the present disclosure in unnecessary detail.

Robotic surgical system 1000 generally includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person, e.g., a surgeon, may be able to telemanipulate robot arms 1002, 1003 in a first operating mode. Robotic surgical system 1000 may be configured for use on a patient 1013 lying on a patient table 1012 to be treated in a minimally invasive manner. Robotic surgical system 1000 may further include a database 1014, in particular coupled to control device 1004, in which are stored, for example, pre-operative data from patient 1013 and/or anatomical atlases.

Each of the robot arms 1002, 1003 may include a plurality of members, which are connected through joints, and mounted device which may be, for example, a surgical tool "ST." One or more of the surgical tools "ST" may be instrument 10 (FIG. 1A), thus providing such functionality on a robotic surgical system 1000.

Robot arms 1002, 1003 may be driven by electric drives, e.g., motors, connected to control device 1004. Control device 1004, e.g., a computer, may be configured to activate the motors, in particular by means of a computer program, in such a way that robot arms 1002, 1003, and, thus, their mounted surgical tools "ST" execute a desired movement and/or function according to a corresponding input from manual input devices 1007, 1008, respectively. Control device 1004 may also be configured in such a way that it regulates the movement of robot arms 1002, 1003 and/or of the motors.

Figure 8:
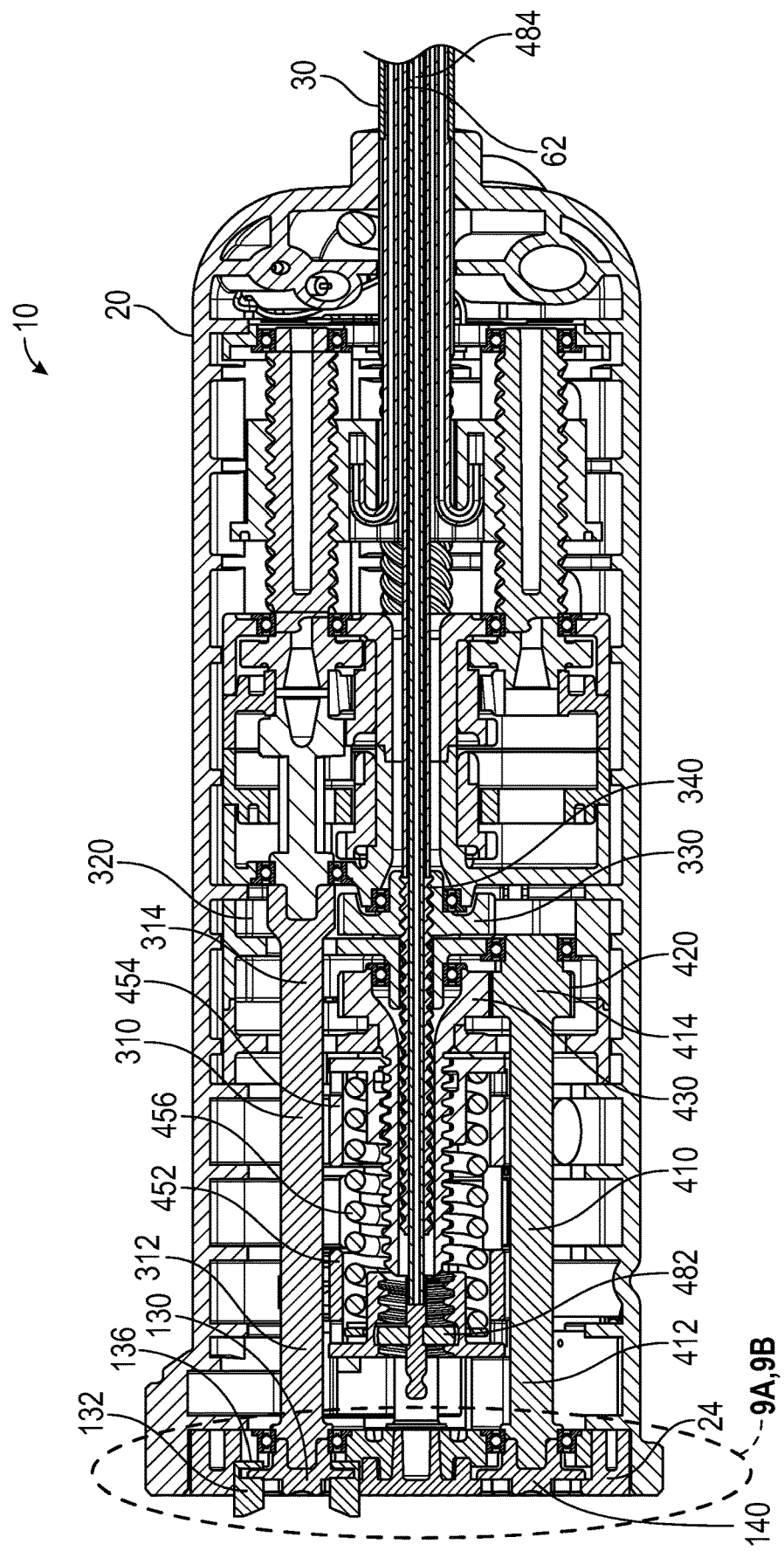
FIG. 8 is a transverse, cross-sectional view taken along section line "8-8" of FIG. 2B.
Figure 9A:
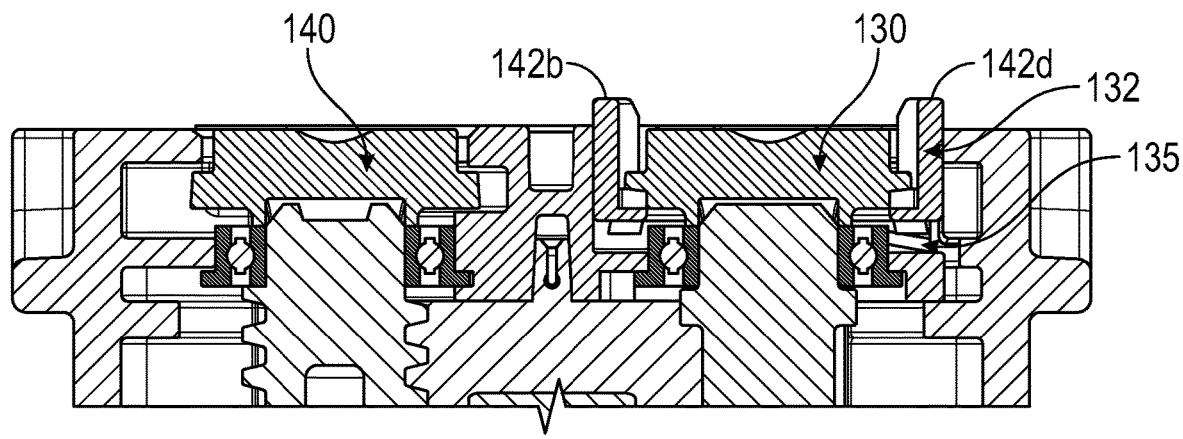
FIG. 9A is an enlarged, perspective view of the area of detail "9A" in FIG. 8 illustrating the knife blade lock in a locked position.
Figure 9B:
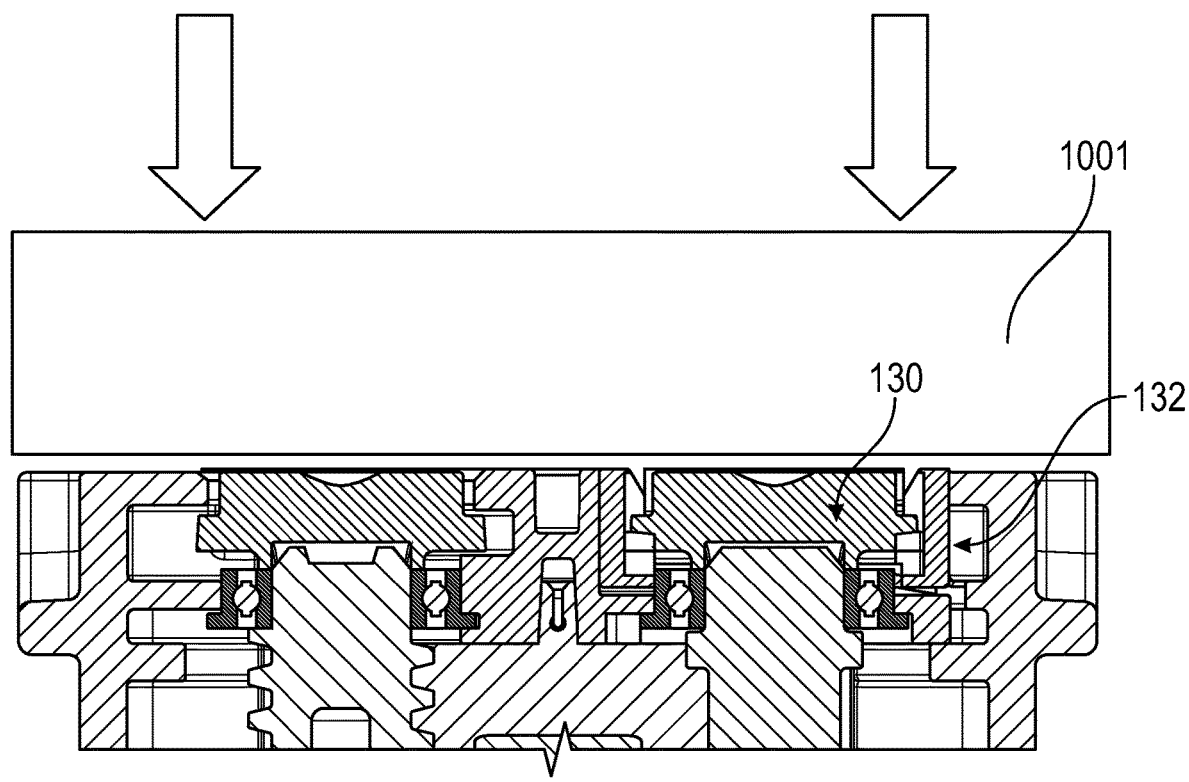
FIG. 9B is an enlarged, perspective view of the area of detail "9B" in FIG. 8 illustrating an instrument interface of the exemplary robotic surgical system of FIG. 4 operably coupling with a proximal portion of the instrument of FIG. 1 to transition the knife blade lock towards an unlocked position.

With reference to FIGS. 5-9B, a knife blade lock 132 is operably coupled to third drive input 130 and serves to prevent manipulation of knife tube 62 and thus, movement of knife blade 64 between jaw members 42, 44 until gearbox assembly 100 is operably interfaced with a suitable instrument interface of robotic surgical system 1000 (e.g., robotic surgical system 1000 shown in FIG. 4 may include an instrument interface 1001 shown schematically in FIG. 9B) to provide rotational input to drive inputs 110-140. Knife blade lock 132 includes an annular body portion 136 disposed within housing 20. The annular body portion 136 defines an aperture 134 therethrough configured to receive a pair of distally extending fingers 126a, 126b of drive input 130 therethrough. A plurality of protrusions, e.g., four (4) protrusions 142a-d, extend proximally from annular body portion 136 through the aperture defined in proximal face plate 24 through which drive input 130 extends. A plurality of teeth 138 are defined along an inner surface of body portion 136 and are configured to releasably interlock with a plurality of teeth 128 defined by drive input 130 to prevent rotation of drive input 130. The knife blade lock 132 is movable relative to proximal face plate 24 between a locked position (FIG. 9A) and an unlocked position (FIG. 9B). As shown in FIGS. 8 and 9A, knife blade lock 132 is biased proximally into the locked position by a biasing member 135 (e.g., a wave spring, a coil spring, or the like) operably coupled to knife blade lock 132 and disposed within housing 20. When knife blade lock 132 is in the locked position, teeth 128 of drive input 130 are interlocked with teeth 138 of knife blade lock 132 to prevent rotation of drive input 130 and protrusions 142a-d extend distally from proximal face plate 24. When knife blade lock 132 is in the unlocked position, protrusions 142a-d are depressed into the aperture defined in proximal face plate 24 through which protrusions 142a-d extend to move teeth 138 of knife blade lock 132 out of interlocking engagement with teeth 128 of drive input 130 such that drive input 130 is free to rotate and drive rotation of input shaft 310. As shown in FIG. 9B, surgical instrument 10 may be operably coupled to robotic surgical system 1000 via coupling of a proximal portion of surgical instrument 10, including proximal face plate 24, to instrument interface 1001, which causes instrument interface 1001 to engage and depress protrusions 142a-d against the bias of biasing member 135 into the aperture defined in proximal face plate 24 through which protrusions 142a-d extend, thereby moving knife blade lock 132 distally to move teeth 138 of knife blade lock 132 distally and out of interlocking engagement with teeth 128 of drive input 130. With teeth 138 of knife blade lock 132 out of interlocking engagement with teeth 128 of drive input 130, drive input 130 is free to rotate and drive rotation of input shaft 310 to manipulate knife tube 62 to move knife blade 64 (FIG. 1B) between jaw members 42, 44 to cut tissue grasped between tissue-contacting surfaces 46, 48. Upon decoupling of instrument interface 1001 from surgical instrument 10, the bias of biasing member 135 imparted on knife blade lock 132 returns knife blade lock 132 to the locked position. In this manner, knife blade 64 will not be permitted to move prior to interfacing surgical instrument 10 with robotic surgical system 1000. As those skilled in the art will appreciate, preventing inadvertent movement and/or exposure of the knife blade 64 will serve to prevent medical staff from being cut by the knife blade 64 during transit and/or handling of surgical instrument 10. In some embodiments, teeth 128 and/or teeth 138 may have a tapered ramp configuration such that, should inadvertent movement and/or exposure of knife blade 64 occur, drive input 130 can be rotated relative to knife blade lock 132 to move the knife blade 64 out of an exposed position (e.g., between jaw members 42, 44) while knife blade lock 132 is in the locked position.

With reference to FIGS. 2A-3 and 8, jaw drive sub-assembly 400 of gearbox assembly 100 is shown generally including an input shaft 410, an input gear 420, a drive gear 430, a thumbwheel 440, and a spring force assembly 450.

Input shaft 410 includes a proximal end portion 412 operably coupled to fourth drive input 140 and a distal end portion 414 having input gear 420 engaged thereon such that rotational input provided to fourth drive input 140 drives rotation of input shaft 410 to, thereby, drive rotation of input gear 420. Input gear 420 is disposed in meshed engagement with drive gear 430 such that rotation of input gear 420, e.g., in response to a rotational input provided at fourth drive input 140, effects rotation of drive gear 430 in an opposite direction. Thumbwheel 440 is also disposed in meshed engagement with drive gear 430 such that rotation of thumbwheel 440 effects rotation of drive gear 430 in an opposite direction, thus enabling manual driving of drive gear 430 via manipulation of thumbwheel 440. Drive rod 484 includes a distal end portion operably coupled to cam-slot assembly 52 of end effector assembly 40 (FIG. 1A). Drive rod 484 extends proximally through shaft 30, housing 20, and gearbox assembly 100 (see FIG. 8).

Turning to FIGS. 3 and 8, knife drive sub-assembly 300 includes an input shaft 310, an input gear 320, a central gear 330 defining external threading and internal threading, and a lead screw 340. Input shaft 310 extends parallel and offset relative to input shaft 410 and includes a proximal end portion 312 operably coupled to third drive input 130 of gearbox assembly 100 (FIGS. 2A and 2B) and a distal end portion 314 having input gear 320 engaged thereon such that rotational input provided to third drive input 130 drives rotation of input shaft 310 when knife blade lock 132 is in the unlocked position to, thereby, drive rotation of input gear 320. Input gear 320 is disposed in meshed engagement with the external threading of central gear 330. Central gear 330 is coaxial with and positioned distally of drive gear 430. Lead screw 340 extends through central gear 330 and is threadingly engaged with the internal threading thereof such that rotation of central gear 330, e.g., in response to a rotational input provided to third drive input 130, translates lead screw 340. Lead screw 340 is fixedly engaged about a proximal end portion of knife tube 62 such that translation of lead screw 340 translates knife tube 62 to thereby move the knife blade 64 between jaw members 42, 44 (FIGS. 1A and 1B). Lead screw 340 and knife tube 62 are coaxially disposed about drive rod 484. When knife blade lockout 132 is in the locked position, third drive input 130 is unable to rotate due to interlocking engagement between teeth 138 of knife blade lock 132 and thus, third drive input 130 is prevented from driving rotation of input shaft 310 to move knife blade 64 between jaw members 42, 44 (FIGS. 1A and 1B).

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical instrument for use with a robotic surgical system, comprising:
   a housing;
   a shaft extending distally from the housing;
   a pair of jaw members disposed at a distal end of the shaft and configured to grasp tissue;
   a knife blade configured to cut tissue grasped between the pair of jaw members;
   a drive input disposed within the housing and configured to receive an input from the robotic surgical system to translate the knife blade;
   a knife blade lock operably coupled to the drive input and defining an aperture through which at least a portion of the drive input extends, the knife blade lock configured to transition between a locked configuration wherein the knife blade lock engages the drive input to prevent the drive input from causing translation of the knife blade and an unlocked configuration wherein the knife blade lock is disengaged from the drive input to permit the drive input to cause translation of the knife blade;
   an input shaft operably coupled to the drive input, the drive input configured to cause the input shaft to translate the knife blade in response to the input received by the drive input from the robotic surgical system; and
   a gearbox assembly including:
      an input gear engaged to a distal end portion of the input shaft, wherein the input provided to the drive input from the robotic surgical system drives rotation of the input shaft when the knife blade lock is in the unlocked configuration to drive rotation of the input gear;
      a central gear defining an internal threading and an external threading in meshed engagement with the input gear; and
      a lead screw extending through the central gear and threadingly engaged with the internal threading of the central gear, wherein rotation of the central gear in response to the input provided to the drive input from the robotic surgical system translates the lead screw to translate the knife blade.

2. The surgical instrument according to claim 1, further comprising a biasing member disposed within the housing and operably coupled to the knife blade lock, the biasing member configured to bias the knife blade lock into the locked configuration.

3. The surgical instrument according to claim 1, wherein the knife blade lock includes an annular body portion surrounding the aperture.

4. The surgical instrument according to claim 3, wherein the knife blade lock includes a plurality of protrusions extending from the annular body portion.

5. The surgical instrument according to claim 4, wherein the plurality of protrusions extend proximally from a proximal end of the housing when the knife blade lock is in the locked configuration.

6. The surgical instrument according to claim 1, wherein the knife blade lock defines a plurality of teeth configured to interlock with a plurality of teeth defined by the drive input when the knife blade lock is in the locked configuration.

7. The surgical instrument according to claim 1, wherein the knife blade lock is configured to be contacted by a surgical instrument interface of the robotic surgical system upon coupling of the surgical instrument to the robotic surgical system to transition the knife blade lock to the unlocked configuration.

8. The surgical instrument according to claim 1, wherein the shaft includes an articulating section configured to articulate the pair of jaw members.

9. A surgical instrument for use with a robotic surgical system, comprising:
- a knife blade configured to cut tissue;
- a knife tube coupled to the knife blade and configured to translate to move the knife blade for cutting tissue;
- a drive input configured to receive an input from the robotic surgical system;
- a knife blade lock operably coupled to the drive input and defining an aperture through which at least a portion of the drive input extends, the knife blade lock configured to transition between a locked configuration wherein the knife blade lock engages the drive input to prevent the drive input from causing translation of the knife tube and an unlocked configuration wherein the knife blade lock is disengaged from the drive input to permit the drive input to cause translation of the knife tube; and
- wherein the knife blade lock includes an annular body portion surrounding the aperture, wherein the knife blade lock includes a plurality of protrusions extending from the annular body portion and wherein the plurality of protrusions each extend proximally from a proximal end of a housing when the knife blade lock is in the locked configuration.

10. The surgical instrument according to claim 9, further comprising an input shaft operably coupled to the drive input, the drive input configured to cause the input shaft to translate the knife tube in response to the input received by the drive input from the robotic surgical system.

11. The surgical instrument according to claim 10, further comprising a gearbox assembly including:
- an input gear engaged to a distal end portion of the input shaft, wherein the input provided to the drive input from the robotic surgical system drives rotation of the input shaft when the knife blade lock is in the unlocked configuration to drive rotation of the input gear;
- a central gear defining an internal threading and an external threading in meshed engagement with the input gear; and
- a lead screw extending through the central gear and threadingly engaged with the internal threading of the central gear, wherein rotation of the central gear in response to the input provided to the drive input from the robotic surgical system translates the lead screw to translate the knife tube.

12. The surgical instrument according to claim 9, further comprising a biasing member operably coupled to the knife blade lock and configured to bias the knife blade lock into the locked configuration.

13. The surgical instrument according to claim 9, wherein the knife blade lock defines a plurality of teeth configured to interlock with a plurality of teeth defined by the drive input when the knife blade lock is in the locked configuration.

14. The surgical instrument according to claim 9, wherein the knife blade lock is configured to be contacted by a surgical instrument interface of the robotic surgical system upon coupling of the surgical instrument to the robotic surgical system to transition the knife blade lock to the unlocked configuration.

15. The surgical instrument according to claim 9, wherein the portion of the drive input that extends through the aperture defined by the knife blade lock includes a distally-extending finger.

16. A surgical instrument for use with a robotic surgical system, comprising:
- an end effector assembly;
- a knife blade configured to translate through the end effector assembly to cut tissue;
- a drive input configured to receive an input from the robotic surgical system to translate the knife blade; and
- a knife blade lock defining an aperture through which at least a portion of the drive input extends, wherein the knife blade lock is configured to releasably engage the drive input to prevent the drive input from causing translation of the knife blade, and wherein the knife blade lock defines a plurality of teeth configured to interlock with a plurality of teeth defined by the drive input when the knife blade lock is in a locked configuration.

\* \* \* \* \*